(12) United States Patent
Stasko et al.

(10) Patent No.: US 9,669,041 B2
(45) Date of Patent: Jun. 6, 2017

(54) NITRIC OXIDE RELEASING BATH COMPOSITIONS AND METHODS OF USING THE SAME

(71) Applicant: Novan, Inc., Durham, NC (US)

(72) Inventors: Nathan Stasko, Durham, NC (US); Ryan Doxey, Raleigh, NC (US)

(73) Assignee: Novan, Inc., Morrisville, NC (US)

( * ) Notice: Subject to any disclaimer, the term of this patent is extended or adjusted under 35 U.S.C. 154(b) by 77 days.

(21) Appl. No.: 14/353,599

(22) PCT Filed: Oct. 26, 2012

(86) PCT No.: PCT/US2012/062051
§ 371 (c)(1),
(2) Date: Apr. 23, 2014

(87) PCT Pub. No.: WO2013/063354
PCT Pub. Date: May 2, 2013

(65) Prior Publication Data
US 2014/0255318 A1  Sep. 11, 2014

Related U.S. Application Data

(60) Provisional application No. 61/552,395, filed on Oct. 27, 2011.

(51) Int. Cl.
| | | |
|---|---|---|
| *A61K 49/00* | (2006.01) | |
| *A61K 31/695* | (2006.01) | |
| *A01N 59/00* | (2006.01) | |
| *A61K 33/00* | (2006.01) | |
| *A61Q 19/10* | (2006.01) | |
| *A61K 8/19* | (2006.01) | |
| *A61K 8/40* | (2006.01) | |

(52) U.S. Cl.
CPC ............ *A61K 31/695* (2013.01); *A01N 59/00* (2013.01); *A61K 8/19* (2013.01); *A61K 8/40* (2013.01); *A61K 33/00* (2013.01); *A61Q 19/10* (2013.01)

(58) Field of Classification Search
USPC ........................................................ 424/10.1
See application file for complete search history.

(56) References Cited

U.S. PATENT DOCUMENTS

| | | | |
|---|---|---|---|
| 4,366,169 A * | 12/1982 | White | A61K 31/02 424/DIG. 13 |
| 4,650,667 A | 3/1987 | Eguchi et al. | |
| 4,666,707 A | 5/1987 | Eguchi et al. | |
| 5,002,758 A * | 3/1991 | Ichii | A61K 8/046 424/44 |
| 5,110,603 A | 5/1992 | Rau | |
| 5,958,462 A | 9/1999 | McLean | |
| 5,997,901 A * | 12/1999 | Mills | A61K 8/02 424/400 |
| 6,121,215 A | 9/2000 | Rau | |
| 6,793,644 B2 | 9/2004 | Stenzler | |
| 2002/0098208 A1 | 7/2002 | Wooley et al. | |
| 2002/0114850 A1 | 8/2002 | Camper et al. | |
| 2006/0102656 A1 | 5/2006 | Troost et al. | |
| 2006/0241546 A1 | 10/2006 | Alimi | |
| 2006/0269620 A1 | 11/2006 | Morris et al. | |
| 2009/0088484 A1 | 4/2009 | Mohanty | |
| 2009/0214618 A1 | 8/2009 | Schoenfisch et al. | |
| 2010/0098733 A1 | 4/2010 | Stasko | |
| 2010/0239512 A1 | 9/2010 | Morris et al. | |
| 2010/0331968 A1 | 12/2010 | Morris et al. | |
| 2011/0052650 A1 | 3/2011 | Morris et al. | |
| 2011/0086234 A1 | 4/2011 | Stasko et al. | |
| 2011/0250151 A1 | 10/2011 | Mateu et al. | |
| 2012/0136323 A1 | 5/2012 | Stasko et al. | |

FOREIGN PATENT DOCUMENTS

| | | |
|---|---|---|
| WO | WO 2008/112940 A1 | 9/2008 |
| WO | WO 2012/100174 A1 | 7/2012 |
| WO | WO 2013/029009 A1 | 2/2013 |

OTHER PUBLICATIONS

Augsberger (Journal of pharmaceutical sciences. Apr. 1, 1966;55(4):418-23).*
Ghaffari (Nitric Oxide 14 (2006) 21-29).*
Notification of Transmittal of the International Search Report and the Written Opinion of the International Searching Authority, or the Declaration corresponding to International Application No. PCT/US2012/062051 mailed Feb. 28, 2013.
Baroli, "Penetration of Nanoparticles and Nanomaterials in the Skin: Fiction or Reality?", *Journal of Pharmaceutical Sciences*, Jan. 2010, vol. 99, No. 1.
Dinh et al. "Effect of Hydrophobic Structure on the Catalysis of Nitric Oxide Release from Zwitterionic Diazeniumdiolates in Surfactant and Liposome Media", *Nitric Oxide: Biology and Chemistry*, 2005, 13, 204-209.
International Preliminary Report on Patentability corresponding to International Application No. PCT/US2012/062051 mailed May 8, 2014.
Price et al. "Micellar Catalysis of Nitric Oxide Dissociation from Diazeniumdiolates", *Langmuir*, 2003, 19, 2096-2102.
Schaffer MR, et al. "Diabetes-Impaired Healing and Reduced Wound Nitric Oxide Synthesis: A Possible Pathophysiologic Correlation", *Surgery*, 1997, 121(5):513-9.
Shi HP, et al. "The Role of iNOS in Wound Healing", *Surgery*, 2001, 130(2):225-9.

* cited by examiner

*Primary Examiner* — Devang Thakor
(74) *Attorney, Agent, or Firm* — Myers Bigel, P.A.

(57) ABSTRACT

The present invention relates to bath compositions that may release nitric oxide when combined with an aqueous solution, thereby producing a nitric oxide releasing soak and/or bath. The present invention also relates to methods of using nitric oxide releasing bath compositions.

19 Claims, 2 Drawing Sheets

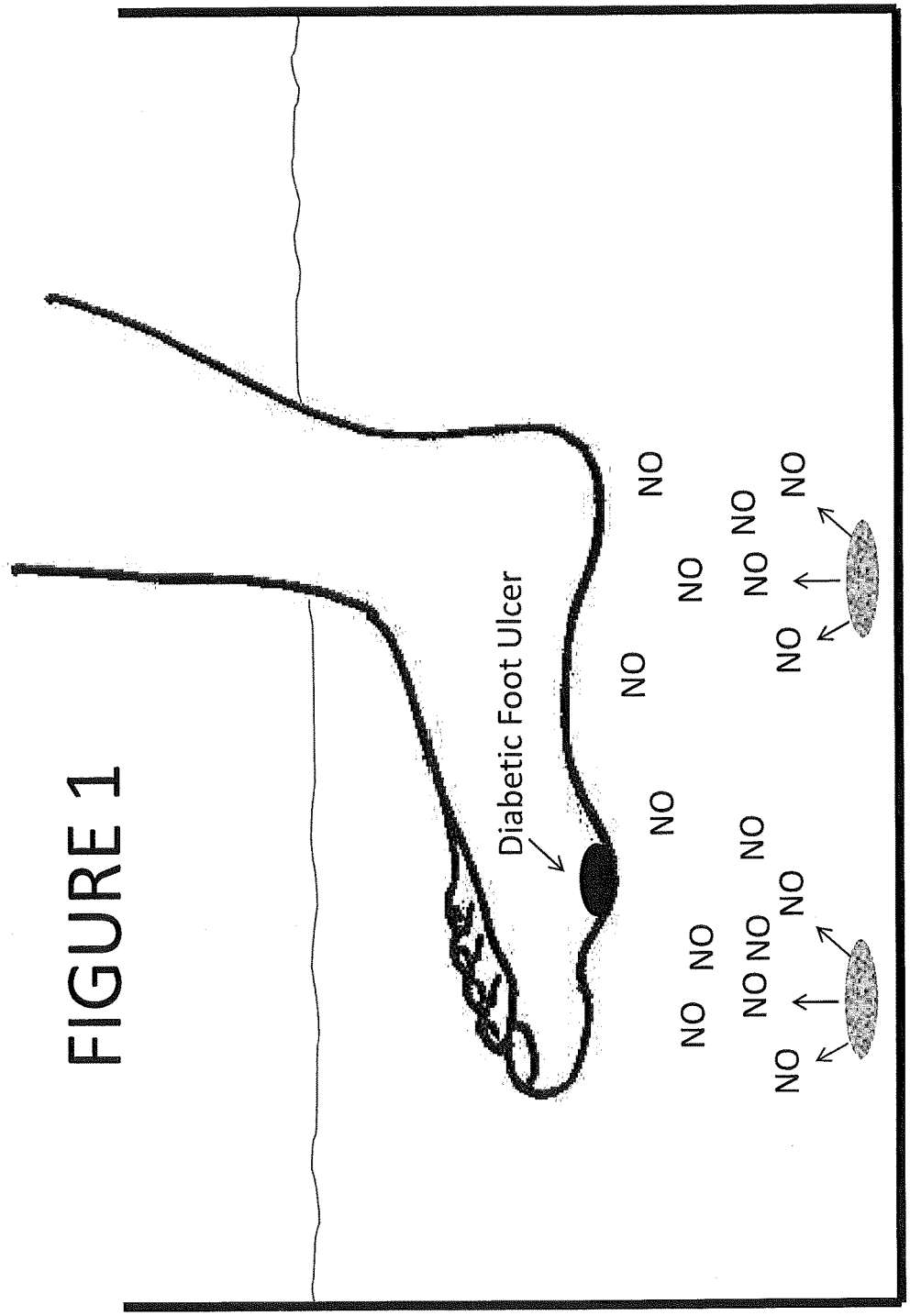

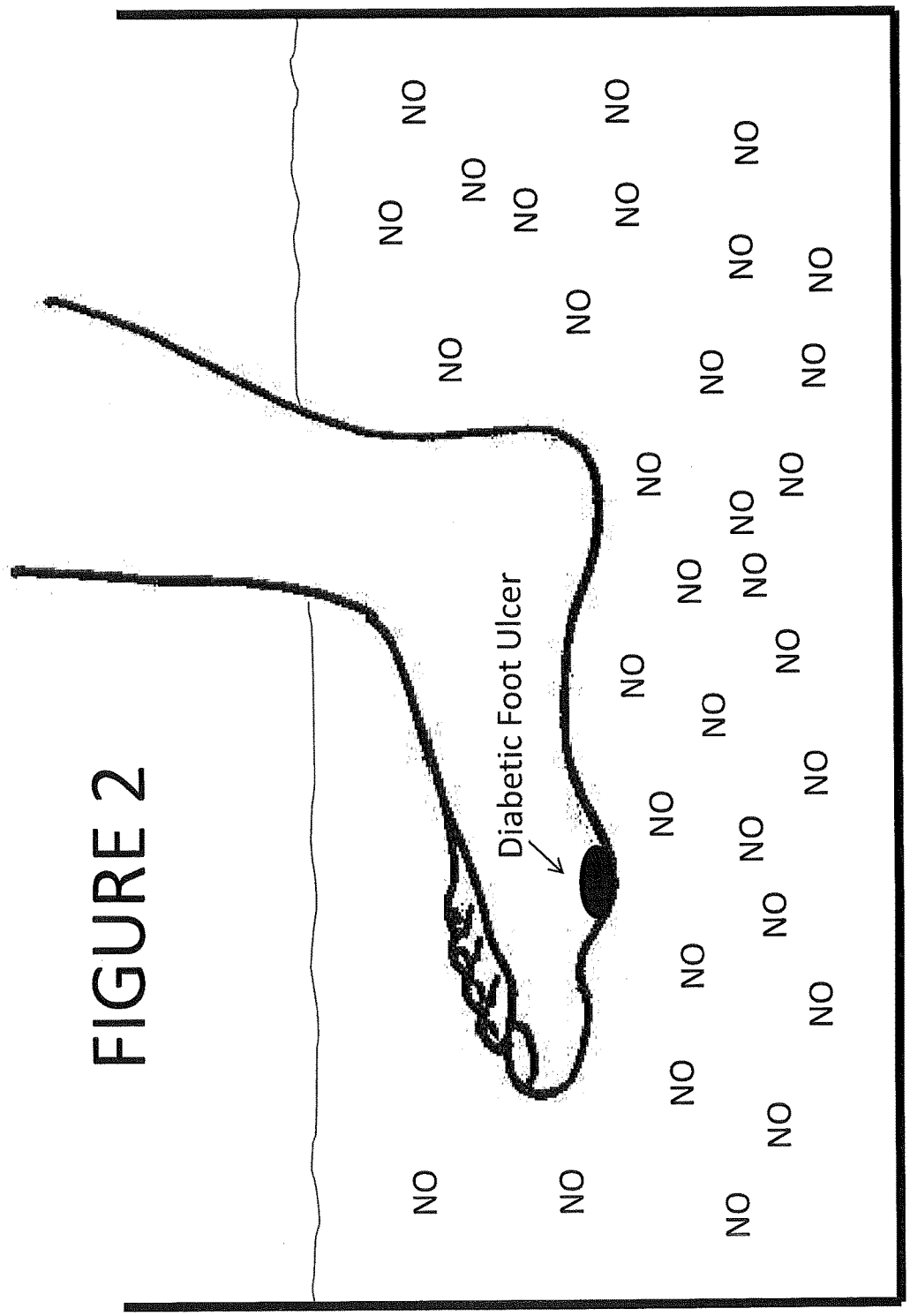

NITRIC OXIDE RELEASING BATH COMPOSITIONS AND METHODS OF USING THE SAME

RELATED APPLICATION DATA

This application is a 35 U.S.C. 371 national stage application of PCT International Application No. PCT/US2012/062051, filed on Oct. 26, 2012, which claims priority to U.S. Provisional Patent Application Ser. No. 61/552,395, filed on Oct. 27, 2011, the disclosures of which are incorporated herein by reference in their entireties. The above-referenced PCT International Application was published as International Publication No. WO 2013/063354 A1 on May 2, 2013.

FIELD OF THE INVENTION

The present invention relates to bath compositions that may release nitric oxide when combined with an aqueous solution, thereby producing a nitric oxide releasing soak and/or bath. The present invention also relates to methods of using nitric oxide-releasing bath compositions.

BACKGROUND OF THE INVENTION

Bath therapies can be used to relieve various aches, pains, and topical ailments by immersing a portion of a subject's body into the bath or soak. The skin may benefit from a soak as the soak can stimulate the skin, provide relief from skin irritations, such as itching, and/or provide moisture to the skin. In some instances, therapeutic agents may also be added to a bath or soak to provide a subject with further therapeutic benefits.

It is known that nitric oxide possesses a broad-spectrum of antimicrobial activity and may be used as an alternative to conventional antibiotics for drug resistant bacteria. Furthermore, some recent studies have demonstrated that nitric oxide may also play an important role in the wound healing process by promoting angiogenesis through stimulation of vascular endothelial growth factor (VEGF) and increase fibroblast collagen synthesis. See Schaffer M R, et al., *Diabetes-impaired healing and reduced wound nitric oxide synthesis: A possible pathophysiologic correlation.* Surgery 1997; 121(5):513-9; and Shi H P, et al., *The role of iNOS in wound healing.* Surgery 2001; 130 (2):225-9. Furthermore, nitric oxide has been shown to have other beneficial properties, including reducing inflammation and participation in wound healing biochemical cascades.

SUMMARY OF THE INVENTION

Provided according to some embodiments of the invention are compositions that include at least one nitric oxide (NO)-releasing compound. In some embodiments, the at least one NO-releasing compound releases NO upon reaction with water. Further, in some embodiments, the at least one NO-releasing compound includes at least one NO-releasing macromolecule, such as, for example, NO-releasing co-condensed silica.

Also provided are methods of treating a subject that include contacting a bath composition according to an embodiment of the invention with an aqueous solution to form NO, thereby producing a nitric oxide releasing bath; and exposing at least a portion of the subject to the bath.

Further provided are methods of cleaning and/or disinfecting an article, device and/or instrument that include contacting a bath composition according to an embodiment of the invention, with an aqueous solution to form NO, thereby producing a NO-releasing bath; and exposing at least a portion of the article, device and/or instrument to the bath.

In addition, provided are methods of providing NO to a plant that include contacting a bath composition according to an embodiment of the invention with an aqueous solution to form NO, thereby producing a NO-releasing bath, and contacting at least a portion of the plant to the NO-releasing bath.

Also provide according to embodiments of the invention are methods of treating a subject that include contacting a bath composition according to an embodiment of the invention with an aqueous solution to form a bath solution; optionally heating the bath solution, and exposing at least a portion of the subject to the bath. Further provided according to embodiments of the invention are methods of cleaning an article, device and/or instrument that include contacting a bath composition according to an embodiment of the invention with an aqueous solution to form a bath solution; optionally heating the bath solution, and exposing at least a portion of the article, device and/or instrument to the bath.

BRIEF DESCRIPTION OF THE FIGURES

The foregoing and other objects, features and advantages of the invention will become more apparent from the following more particular description of exemplary embodiments of the invention and the accompanying drawings. The drawings are not necessarily to scale, emphasis instead being placed upon illustrating the principles of the invention.

FIG. 1 is a diagram of a bath/soak according to some embodiments of the present invention.

FIG. 2 is a diagram of a bath/soak according to further embodiments of the present invention.

DETAILED DESCRIPTION OF THE INVENTION

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value, such as, for example, an amount or concentration, is meant to encompass variations of ±20%, ±10%, ±5%, ±1%, ±0.5%, or even ±0.1% of the specified amount. A range provided herein for a measureable value may include any other range and/or individual value therein.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain Exemplary branched alkyl groups include, but are not limited to, isopropyl, isobutyl, tert-butyl. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-5}$ straight-chain alkyls. In other embodiments, "alkyl" refers, in particular, to $C_{1-5}$ branched-chain alkyls.

Alkyl groups may optionally be substituted (a "substituted alkyl") with one or more alkyl group substituents, which may be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There may be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that may be a single aromatic ring, or multiple aromatic rings that are fused together, linked covalently, or linked to a common group, such as, but not limited to, a methylene or ethylene moiety. The common linking group also may be a carbonyl, as in benzophenone, or oxygen, as in diphenylether, or nitrogen, as in diphenylamine. The term "aryl" specifically encompasses heterocyclic aromatic compounds. The aromatic ring(s) may comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group may be optionally substituted (a "substituted aryl") with one or more aryl group substituents, which may be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —$NR^1R''$, wherein $R^1$ and R" may each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group may be optionally partially unsaturated. The cycloalkyl group also may be optionally substituted with an alkyl group substituent as defined herein, oxo, and/or alkylene. There may be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein may refer to, for example, methoxyl, ethoxyl, propoxyl, isopropoxyl, butoxyl, f-butoxyl, and pentoxyl. The term "oxyalkyl" may be used interchangeably with "alkoxyl". In some embodiments, the alkoxyl has 1, 2, 3, 4, or 5 carbons.

"Aralkyl" refers to an aryl-alkyl group wherein aryl and alkyl are as previously described, and included substituted aryl and substituted alkyl. Exemplary aralkyl groups include, but are not limited to, benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group may be straight, branched or cyclic. The alkylene group also may be optionally unsaturated and/or substituted with one or more "alkyl group substituents." There may be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include, but are not limited to, methylene ($-CH_2-$); ethylene ($-CH_2-CH_2-$); propylene ($-(CH_2)_3-$); cyclohexylene ($-C_6H_{10}-$); $-CH=CH-CH=CH-$; $-CH=CH-CH_2-$; wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($-O-CH_2-O-$); and ethylenedioxyl ($-O-(CH_2)_2-O-$). An alkylene group may have about 2 to about 3 carbon atoms and may further have 6-20 carbons.

"Arylene" refers to a bivalent aryl group. An exemplary arylene is phenylene, which may have ring carbon atoms available for bonding in ortho, meta, or para positions with regard to each other, i.e., respectively. The arylene group may also be napthylene. The arylene group may be optionally substituted (a "substituted arylene") with one or more "aryl group substituents" as defined herein, which may be the same or different.

"Aralkylene" refers to a bivalent group that contains both alkyl and aryl groups. For example, aralkylene groups may have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as $NR_3$, $NH_3$, $NHR_2$, and $NH_2R$, wherein R may be alkyl, branched alkyl, cycloalkyl, aryl, alkylene, arylene, aralkylene. Thus, "amino" as used herein may refer to a primary amine, a secondary amine, or a tertiary amine. In some embodiments, one R of an amino group may be a cation stabilized diazeniumdiolate (i.e., $NONO^-X^+$).

The terms "cationic amine" and "quaternary amine" refer to an amino group having an additional (i.e., a fourth) group, for example a hydrogen or an alkyl group bonded to the nitrogen. Thus, cationic and quarternary amines carry a positive charge.

The term "alkylamine" refers to the -alkyl-$NH_2$ group.

The term "carbonyl" refers to the $-(C=O)-$ group.

The term "carboxyl" refers to the $-COOH$ group and the term "carboxylate" refers to an anion formed from a carboxyl group, i.e., $-COO^-$.

The terms "halo", "halide", or "halogen" as used herein refer to fluoro, chloro, bromo, and iodo groups.

The term "hydroxyl" and "hydroxy" refer to the $-OH$ group.

The term "hydroxyalkyl" refers to an alkyl group substituted with an $-OH$ group.

The term "mercapto" or "thio" refers to the $-SH$ group. The term "silyl" refers to groups comprising silicon atoms (Si).

As used herein the term "alkoxysilane" refers to a compound comprising one, two, three, or four alkoxy groups bonded to a silicon atom. For example, tetraalkoxysilane refers to $Si(OR)_4$, wherein R is alkyl. Each alkyl group may be the same or different. An "alkylsilane" refers to an alkoxysilane wherein one or more of the alkoxy groups has been replaced with an alkyl group. Thus, an alkylsilane comprises at least one alkyl-Si bond. The term "fluorinated silane" refers to an alkylsilane wherein one of the alkyl groups is substituted with one or more fluorine atoms. The term "cationic or anionic silane" refers to an alkylsilane wherein one of the alkyl groups is further substituted with an alkyl substituent that has a positive (i.e., cationic) or a negative (i.e. anionic) charge, or may become charged (i.e., is ionizable) in a particular environment (i.e., in vivo).

The term "silanol" refers to a Si—OH group.

Provided according to some embodiments of the present invention are bath compositions that include at least one nitric oxide (NO)-releasing compound. In some embodiments of the invention, the at least one NO-releasing compound included in the bath composition may release NO upon reaction with water. In other embodiments, the NO-releasing compound may release NO via thermal degradation as a function of temperature of the bath composition. In some embodiments, the at least one NO-releasing compound includes a NO-releasing macromolecule. Furthermore, in some embodiments, the at least one NO-releasing macromolecule includes a diazeniumdiolate functional group. In particular embodiments, the NO-releasing macromolecule includes a diazeniumdiolate-functionalized co-condensed silica.

In some embodiments of the invention, the components of the bath composition are selected based on the properties of the NO-releasing compound and the indication for which the resulting bath is to be used, such that the interaction of the properties of the bath composition, NO-releasing compound, and aqueous environment act to provide the desired NO release profile.

Any suitable NO-releasing compound may be used in bath compositions according to embodiments of the invention. The NO may be released from the NO-releasing compound by any suitable mechanism, including via reaction with water and/or thermal degradation. Examples of NO-releasing functional groups that may be included in the NO-releasing compound include, but are not limited to, diazeniumdiolate, nitrosamine, hydroxyl nitrosamine, nitrosothiol, hydroxylamine, hydroxyurea, metal nitrosyl complexes, and any combination thereof. Other NO-releasing functional groups that are capable of releasing nitric oxide in a therapeutic manner, such as acidified nitrite, may also be utilized.

The NO-releasing compound may be a small molecule, oligomer and/or polymer and may be in any suitable physical form, including, but not limited to, particles, coatings, films, liquids, solutions and the like. In some embodiments, the nitric oxide-releasing compound comprises diazeniumdiolate-functionalized polysiloxane macromolecules as described below. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in U.S. Provisional Patent Application Ser. No. 61/526,918 entitled "TUNABLE NITRIC OXIDE-RELEASING MACROMOLECULES HAVING MULTIPLE NITRIC OXIDE DONOR STRUCTURES"; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, the disclosure of which is incorporated herein by reference in its entirety.

The term "diazeniumdiolate-functionalized co-condensed silica" refers to co-condensed polysiloxane macromolecules functionalized with diazeniumdiolate, such as the NO-releasing particles described in U.S. Publication No. 2009/0214618, the disclosure of which is incorporated by reference herein in its entirety. Such particles may be prepared by methods described therein.

In some embodiments, the diazeniumdiolate-functionalized co-condensed silica may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors.

The co-condensed siloxane network may be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula $Si(OR)_4$, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: $R''-(NH-R')_n-Si(OR)_3$, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl) phenethyltrimethoxysilane (AEMP3); [3-(methylamino)propyl]trimethoxysilane (MAP3); N-butylamino-propyltrimethoxysilane (n-BAP3); t-butylamino-propyltrimethoxysilane (t-BAP3); N-ethylaminoisobutyltrimethoxysilane (EAiB3); N-phenylamino-propyltrimethoxysilane (PAP3); and N-cyclohexylaminopropyltrimethoxysilane (cHAP3).

In some embodiments, the aminoalkoxysilane has the formula: $NH[R'-Si(OR)_3]_2$, wherein R is alkyl and R' is alkylene. In some embodiments, the aminoalkoxysilane may be selected from bis(3-triethoxysilylpropyl)amine, bis-[3-(trimethoxysilyl)propyl]amine and bis-[(3-trimethoxysilyl)propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: $R''-N(NONO^-X^+)-R'-Si(OR)_3$, wherein R is alkyl or silyl, R' is alkylene or aralkylene, R" is alkyl or alkylamine, and $X^+$ is a cation selected from the group consisting of $Na^+$, $K^+$, $Cs^+$, $Li^+$, $NH_4^+$, or other quaternary ammonium cation.

In some embodiments of the invention, the diazeniumdiolate-functional aminoalkoxysilane may be $O^2$-protected prior to the preparation of the nitric oxide releasing macromolecules. Such $O^2$-protected diazeniumdiolate functional aminoalkoxysilanes may have the formula: $R''-N(NONO-R''')-R'-Si(OR)_3$, wherein each R is independently H, alkyl or substituted alkyl, R' is substituted or unsubstituted alkylene, substituted or unsubstituted arylene, substituted or unsubstituted alkylarylene or substituted or unsubstituted arylalkylene, R" is H, alkyl or substituted alkyl and R''' is a protecting group that imparts enzymatic, photolytic, or thiolation triggering mechanisms. Such protecting groups are known to those skilled in the art of forming $O^2$-protected diazeniumdiolates.

The chemical composition of the siloxane network, (e.g., amount or the chemical composition of the aminoalkoxysilane), the porosity of the silica network within the macromolecular structure, the size of the co-condensed silica particles, and the nitric oxide charging conditions (e.g., the solvent and base) may be varied to optimize the amount and duration of nitric oxide release. Thus, in some embodiments, the composition of the silica particles may be modified to regulate the half-life of NO release from silica particles with half-lives of nitric oxide release ranging from slow, defined by $t_{1/2}$ values greater than about 60 minutes to fast, defined by $t_{1/2}$ values ranging from about 30 seconds to about 10 minutes at physiological temperature and pH (37° C. and pH=7.4).

In some embodiments of the invention, the co-condensed siloxane network of nitric oxide releasing silica particles is formed from at least one additional silane that modifies surface charge and/or hydrophilicity/hydrophobicity of the co-condensed silica product which affect the octanol/water partition coefficient of the macromolecular delivery vehicle. These parameters control the route of skin penetration, depth of penetration, and the suspension/diffusion of the diazeniumdiolate-modified polysiloxane macromolecules throughout the aqueous solution. Any suitable alkoxysilane that may impart surface charge to the diazeniumdiolate-modified polysiloxane macromolecule may be used. Thus, in some embodiments, the additional alkoxysilane may include a cationic alkoxysilane such as (2-N-benzylaminoethyl)-3-aminopropyl-trimethoxysilane, hydrocholoride; bis (methoxyethyl)-3-trimethoxysilylpropyl-ammonium chloride; N—N-didecyl-N-methyl-N-(3-trimethoxysilyl) ammonium chloride; N-trimethyoxysilylpropyl-N,N,N-trimethyl ammonium chloride; octadecylbis (triethoxysilylpropyl)-ammonium chloride; and octadecyldimethyl(3-trimethoxysilylpropyl)ammonium chloride. In some embodiments, the additional alkoxysilane may include an anionic alkoxysilanes such as 3-trihydroxysilylpropylmethyl phosphonate, sodium salt and carboxyethylsilanetriol, sodium salt.

Any suitable alkoxysilane that may impart hydrophilic properties to the diazeniumdiolate-modified polysiloxane macromolecule may be used. Alkoxysilanes containing repeat poly(ethylene)oxy groups may be used to increase the wetability of the NO-releasing particles thereby helping to improve biocompatibility upon topical application and also enhance the rate of water uptake into the co-condensed siloxane coating. Surface hydrophilicity may thus be utilized to enhance the NO-release kinetics of the diazeniumdiolated aminoalkoxysilane derivatives. Therefore, in some embodiments, the multifunctional alkoxysilane may include a hydrophilic silane such as N-triethoxysilylpropyl)-O-polyethyleneoxide urethane N-3-[amino(polypropylenoxy)] aminopropyltrimethoxysilane; bis-[3-(triethoxysilylpropoxy)-2-hydroxypropoxy]polyethylene oxide; bis(3-triethoxysilylpropyl)polyethylene oxide (25-30); [hydroxy (polyethyleneoxy)propyl]-triethoxysilane; and 2-[methoxy (polyethyleneoxy)propyl]-trimethoxysilane.

Any suitable alkoxysilane that may impart hydrophobic properties to the diazeniumdiolate-modified polysiloxane macromolecule may be used. Hydrophobic silanes are known to those skilled in the art to increase lipophilicity of particle surfaces. In some embodiments, the additional alkoxysilane may include linear alkyl, branched and cyclic alkylalkoxysilanes having at least three carbon atoms, substituted and unsubstituted phenyl alkoxysilanes, and fluorinated alkoxysilanes. Exemplary fluoroalkoxysilanes may include, but are not limited to, heptadecafluoro-1,1,2-2-tetrahydrodecyl)triethoxysilane, (3,3,3-trifluoropropyl) trimethoxysilane, (perfluoroalkyl)ethyltriethoxysilane, nonafluorohexyltrimethoxysilane, nonafluorohexyltriethoxysilane, (tridecafluoro-1,1,2,2-tetrahydrooctyl)triethoxysilane, and (tridecafluoro-1,1,2,2-tetrahydrooctyl)trimethoxysilane.

The hydrophilicity of the diazeniumdiolate-functionalized polysiloxane macromolecules may be assessed by the use of a water/octanol partition coefficient. See *Octanol-Water Partition Coefficients: Fundamentals and Physical Chemistry, Vol. 2 of Wiley Series in Solution Chemistry*. Chichester: John Wiley & Sons Ltd. (1997), which is herein incorporated by reference in its entirety. For example, hydrophobic diazeniumdiolate-functionalized polysiloxane macromolecules may have a water/octanol partition coefficient in a range from about 0.1 to about 7, and hydrophilic diazeniumdiolate-functionalized polysiloxane macromolecules may have a water/octanol partition coefficient in a range from about −2 to about 0.

In some embodiments of the invention, the hydrodynamic radius of the diazeniumdiolate-functionalized co-condensed silica particles is within a range from about 1 nm to about 1,000 μm or any other range and/or individual value therein, such as, but not limited to, from about 1000 nm to about 10 microns, about 100 nm to about 1,000 μm, or about 1 nm to about 100 nm. In some embodiments, to maximize trans-epidermal skin penetration and enhance nitric oxide delivery to deeper skin structures, the size of the macromolecular scaffold may be selected to be in a range from about 5 nm to about 50 nm. In other embodiments, the macromolecular scaffold may be selected to be in a range from about 101 nm to about 10 μm to selectively accumulate diazeniumdiolate-modified polysiloxane macromolecules in the stratum corneum and limit skin penetration, systemic absorption, and any resulting toxicity of the macromolecular scaffold. In some embodiments, the size of the macromolecule scaffold may be selected to be in a range from about 1 μm to about 100 μm to target skin penetration via the trans-follicular route. Selective delivery to the stratum corneum, epidermis or dermis may be achieved by varying the particle size. Skin naturally has a low permeability to particulate materials and the stratum corneum provides an effective barrier to most inorganic nanosized particles with gold nanoparticles, silver nanoparticles, quantum dots, titanium dioxodie, and zinc oxide being the most extensively studied. See, e.g., Baroli, B., Penetration of Nanoparticles and Nanomaterials in the Skin: Fiction or Reality? *Journal of Pharmaceutical Sciences,* 2009 December; 99:21-50.

The size of the NO-releasing compound may affect the release rate of nitric oxide from in the aqueous bath. Properties of the NO-releasing compound may be controlled to affect the release rate of nitric oxide include altering the surface area and porosity of particulate NO donors and controlling particle size to govern the rate of moisture diffusion throughout the particulate matrix to affect the rate at which the particle itself hydrates.

In some embodiments, the size of the NO-releasing compound may also be adjusted to affect the physical properties of the soak solution. Physical properties that are governed by particle size include segregation of the powdered formulation during packaging or manufacturing, the dispersion quality and rate at which the powder disperses into the aqueous media, fluid dynamics of the NO-releasing macromolecule in a bath solution and settling time of the particulate matter to the bottom of the soak/bath solution (in other words, how long it stays suspended). In specific embodiments, this property may be adjusted to optimize delivery of NO to a body surface, e.g., the bottom of a foot such that the release all comes from the bottom of the soak vessel or container (See, FIG. 1). In other embodiments, the particle size may be small enough to allow for rapid, uniform dispersion for delivery to a total body surface area through the media. In some embodiments, the particle size of the bath composition may be adjusted to match the instructions for adding the powder under turbulent flow conditions capable of dispersing larger macromolecular powders (jets, whirlpool, or under a running faucet) or sprinkled on top of the water which may require relatively small (e.g., <10 μm) particle sizes.

The at least one NO-releasing compound may be present in bath compositions according to embodiments of the invention at any suitable concentration, but in some embodiments, the NO-releasing compounds are present in the bath compositions at a concentration sufficient to increase the rate of wound healing, decrease inflammation and/or exert an antimicrobial effect. For example, in particular embodiments, the concentration of diazeniumdiolate-functionalized co-condensed silica in the bath composition is in a range from about 0.01 percent to about 80 percent w/w. In some embodiments, the concentration of the at least one NO-releasing compound in the composition may be adjusted to modulate the amplitude of nitric oxide release (mol NO/g composition) either by changing the weight percentage in the bath composition or by varying the loading of nitric oxide on a macromolecular scaffold to create a desirable therapeutic outcome.

In some embodiments, the final NO storage per gram of the powdered bath composition may be in a range from about 0.1 pmol NO/g to about 10 mmol NO/g composition or any range and/or therapeutic value therein, such as, but not limited to, from about 0.1 pmol NO/g to about 100 nmol NO/g composition, about 1 nmol NO/g to about 10 mmol NO/g composition, about 1 nmol NO/g composition to about 10 µmol NO/g composition, or about 10 µmol NO/g composition to about 1 mmol NO/g composition. In some embodiments, to reduce inflammation and associated inflammatory response factors, the final NO storage per gram of the bath composition may be in a range from about 1 nmol NO/g composition to about 1 mmol NO/g composition. In some embodiments, to promote wound healing, the final NO storage per gram of the bath composition may be in a range from about 10 nmol NO/g composition to about 5 mmol NO/g composition. In some embodiments, to exert antimicrobial activity, the final NO storage per gram of the bath composition may be in a range from about 10 µmol NO/g composition to about 5 mmol NO/g composition. In some embodiments, to treat biofilms by dispersal, the final NO storage per gram of the bath composition may be in a range from about 1 nmol NO/g composition to about 1 mmol NO/g composition, and in some embodiments, to treat biofilms by direct microbicidal activity, the final NO storage per gram of the bath composition may be in a range from about 100 µmol NO/g composition to about 10 mmol NO/g composition.

In some embodiments, the concentration of NO delivered in the bath solution following mixture depends on the volume of the aqueous medium. The volume of the bath/soak solution changes depending on its application and may range from as small as about 0.05 L to soak medical articles or fingers to as large as an entire Olympic sized swimming pools of about 2,500,000 L capable of treating more than one subject at once. In some embodiments, the overall concentration of NO delivered may be in the range from about 1 µmol NO/L up to about 2.5 mol NO/L. In some embodiments, the total NO delivered in the bath/soak solution is calculated as instantaneous rate or the level of release at a particular time. In other embodiments, the total NO delivered in the bath/soak solution is integrated over time, such as a total release or total release over a time interval. In some embodiments, the total NO delivered is in the range from about 1 mmol NO/L to about 100 mmol NO/L. In some embodiments, the total NO delivered is greater than about 16 mmol NO/L.

As discussed above, the present invention relates to bath compositions that comprise, consist essentially of, or consist of at least one NO-releasing compound, such as, for example, NO-releasing macromolecules including diazeniumdiolate-functionalized co-condensed silica. In certain embodiments of the present invention, diazeniumdiolate-functionalized co-condensed silica are present in the bath composition in a concentration in a range from about 20% to about 70% by weight of the composition or any range and/or individual value therein. In particular embodiments of the present invention, diazeniumdiolate-functionalized polysiloxane macromolecules are present in the bath composition in a concentration of about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, or any range therein.

The bath compositions of the present invention when contacted with an aqueous solution may produce a nitric oxide releasing bath or soak. The term "contact" and grammatical variations thereof, as used herein in reference to the contacting of the bath composition and aqueous solution, is intended to include mixing, adding, dissolving, combining, soaking, suspending, immersing, saturating, dipping, incorporating, wetting, submerging, and/or any variation and/or combination thereof. The bath compositions of the present invention may be contacted with an aqueous solution in any suitable manner. For example, a bath composition may be contacted with an aqueous solution before, during, and/or after the aqueous solution is placed in a vessel or container. The term "aqueous solution," as used herein, refers to any liquid solution comprising water. Exemplary aqueous solutions include, but are not limited to, water, deoxygenated water, saline solutions, acidic or alkaline buffer solutions, and/or any combination thereof.

According to some embodiments of the present invention, the nitric oxide releasing bath may effervesce. Effervescence is the release of a gas, such as carbon dioxide, in an aqueous solution and produces bubbles, fizz, and/or foaming in an aqueous solution. Effervescence may be beneficial in stimulating the skin and may provide relief from fatigue. In some embodiments of the present invention, effervescence may enhance the delivery and/or activity of the nitric oxide. In certain embodiments of the present invention; effervescence provides a delivery mechanism for the nitric oxide to the subject in the bath. In some embodiments of the present invention, effervescence increases the half-life of the nitric oxide in the aqueous solution.

Chemical compounds and/or compositions that may be used to produce effervescence are known in the art and include, but are not limited to, those described in U.S. Pat. Nos. 4,650,667; 4,666,707; 5,110,603; and 6,121,215, which are each incorporated herein by reference in their entirety. For example, effervescence may be produced by combining a carbonate and an acid with an aqueous solution. Exemplary carbonates include, but are not limited to, sodium hydrogen carbonate, sodium carbonate, sodium sesquicarbonate, potassium hydrogen carbonate, potassium carbonate, potassium sesquicarbonate, ammonium hydrogen carbonate, ammonium carbonate, ammonium sesquicarbonate, and any combination thereof. Exemplary acids include, but are not limited to, organic acids such as citric acid, tartaric acid, malic acid, fumaric acid, and phosphoric acid; acidic salts of organic acids; straight-chain aliphatic acids such as acetic acid, propanoic acid, butyric acid and valeric acid; dicarboxylic acids such as oxalic acid, malonic acid, and succinic acid; acidic amino acids such as glutamic acid and aspartic acid; hydroxy acids such as glycolic acid, lactic acid, and α-hydroxy butyric acid; and inorganic acids such as phosphoric acid, potassium dihydrogen phosphate, sodium dihydrogen phosphate, sodium sulfite, potassium sulfite, and sulfamic acid; and any combination thereof.

In certain embodiments of the present invention, a carbonate may be present in the bath composition at a concentration in a range from about 25% to about 65% by weight of the composition or any range and/or individual value therein. For example a carbonate may be present in the bath composition at a concentration of about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65% by weight or any range therein. In some embodiments, an acid is present in the bath composition at a concentration from about 0.1% to about 15% by weight of the composition or any range therein and/or individual value therein. For example, in some embodiments, an acid is present in the bath composition at a concentration of about 0.1%, 0.25%, 0.5%, 0.75%, 1%, 2%, 3%, 4%, 5% by weight, or any range therein. In particular embodiments of the present invention, the bath composition includes sodium bicarbonate and citric acid and/or tartaric acid.

In some embodiments of the present invention, the bath composition includes diazeniumdiolate-functionalized polysiloxane macromolecules at a concentration in a range from about 45% to about 55% by weight; sodium bicarbonate at a concentration in a range from about 40% to about 50% by weight; and citric acid and/or tartaric acid at a concentration in a range from about 0.2% to about 2% by weight.

In some embodiments of the invention, an aromatherapy agent is present in the bath compositions. Any suitable concentration may be used, but in some embodiments, the aromatherapy agent is present in the bath composition at a concentration in a range from about 0.1% to about 10% by weight of the composition or any range and/or individual value therein. In certain embodiments of the present invention, an aromatherapy agent is present in an amount of about 0.1%, 0.25%, 0.5%, 0.75%, 1%, 2%, 3%, 4%, 5%, 6%, 7%, 8%, 9%, 10% by weight, or any range therein. Exemplary aromatherapy agents include, but are not limited to, menthol, camphor, jasmine, rosewood oil, eucalyptus oil, sandalwood oil, ylang ylang oil, lavender oil, patchouli oil, wintergreen oil, clove oil, nutmeg oil, aniseed oil, vanilla bean oil, thyme oil, mint oil, sassafras oil, rose oil, orange oil, lavandin oil, chamomile oil, rosemary oil, and any combination thereof. In particular embodiments of the present invention, the bath composition comprises menthol and/or camphor, optionally at a concentration in a range from about 0.1% to about 1% by weight.

In some embodiments of the invention, a glidant is present in the bath compositions. Any suitable concentration of glidant may be used, but in some embodiments, the glidant is present in the bath compositions at a concentration in a range from about 0.1% to about 10% by weight of the composition or any range and/or individual value therein. In certain embodiments of the present invention, a glidant is present in an amount of about 0.1%, 0.25%, 0.5%, 0.75%, 1%, 2%, 3%, 4%, 5%, 6%, 7%, 8%, 9%, 10% by weight, or any range therein. Exemplary glidants include, but are not limited to; colloidal silicon dioxide, talc, calcium silicate, fumed silica, precipitated silica, hydrated silica, aluminum starch octenylsuccinate, stearic acid, magnesium stearate, calcium stearate, and any combination thereof. In particular embodiments of the present invention, the bath composition comprises colloidal silicon dioxide and/or talc, optionally at a concentration in a range from about 0.1% to about 5% by weight.

In some embodiments, inert filler is present in the bath compositions of the present invention. Any suitable concentration of inert filler may be present, but in some embodiments, inert filler is present at a concentration in a range from about 0.1% to about 75% by weight of the composition or any range and/or any individual value therein. In certain embodiments of the present invention, an inert filler is present in an amount of about 0.1%, 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% by weight, or any range therein. Exemplary inert fillers include, but are not limited to, microcrystalline cellulose, lactose, dextrin, dextrose monohydrate, starch, dibasic calcium phosphate dehydrate, sucrose, saccharides, oatmeal milled ultrafine, crystalline sorbitol, magnesium oxide, calcium sulfate dehydrate, carboxymethyl starch, polyacrylate copolymers, and polymethacrylate. In particular embodiments of the present invention, the bath composition comprises microcrystalline cellulose and/or lactose, optionally at a concentration in a range from about 0.5% to about 50% by weight Other components, such as a colorant, an emollient, a surfactant, a moisturizer, a humectant, a sunscreen, an anti-caking agent, a skin protectant, a softening agent, and/or a pH modifying agent, may optionally be added to the bath compositions of the present invention. Exemplary humectants include, but are not limited to, polyethylene glycol, glycerin, polyvinyl alcohol, sorbitol, polyvinylpyrollidone, and any combination thereof. Exemplary emollients include, but are not limited to, mineral oils, fatty acid esters, fatty alcohols, dimethicones, isopropyl palmitate, and any combination thereof. Exemplary surfactants include, but are not limited to, sodium dodecyl sulfate, sodium stearoyl lactylate, sodium laureth sulfate, lauramide DEA, sodium methyl cocoyl taurate, cocamidopropyl betaine, and any combination thereof. Exemplary moisturizers include, but are not limited to, aloe vera, polydimethysiloxane, panthenol, collinsonia Canadensis, wheatgrass extract, oatmeal milled ultrafine, and any combination thereof.

In some embodiments of the present invention, a pH modifying agent may be used to control and/or stabilize the pH of the bath or soak. A pH modifying agent may be used to increase or decrease the pH of the bath or soak. Exemplary pH modifying agents include, but are not limited to, acidic compounds such as p-anisic acid and citric acid; basic compounds such as calcium hydroxide, sodium hydroxide, sodium carbonate, and triethanolamine; and organic and inorganic salts such as sodium bicarbonate, magnesium sulfate, and pentasodium triphosphate.

A colorant may be present in the bath compositions of the present invention to impart a color to the nitric oxide releasing bath. In some embodiments of the present invention, a colorant may provide a color to the bath throughout the duration of the bath. In other embodiments, a colorant may provide a color to the bath solution that fades and/or changes over time. The color of the bath may fade and/or change to provide a visual indicator. The visual indicator may indicate the end of nitric oxide release, the concentration of nitric oxide and/or nitrous acid, a change in temperature, a change in pH, and/or any combination thereof. In certain embodiments of the present invention, the color of the bath may fade and/or change after a specific duration of time. In, another aspect of the present invention, a colorant may be present in the bath composition to delineate the order of operation for the addition of the components of the bath composition and/or to delineate the order of the steps in the methods of treatment of the present invention.

Additional optional components of the bath compositions of the present invention may include excipients that facilitate the formation of an emulsion when an aqueous solution is contacted with a bath composition of the present invention. Thus, a self-emulsifying delivery system may be provided by the bath compositions of the present invention. In other embodiments of the present invention, excipients that enhance and/or accelerate nitric oxide donor lifetime in solution may be included in the bath compositions of the present invention. These excipients may provide enhanced delivery of the nitric oxide to the subject. See, e.g., Bach T., et al., "Effect of Hydrophobic Structure on the Catalysis of Nitric Oxide Release from Zwitterionic Diazeniumdiolates in Surfactant and Liposome Media" *Nitric Oxide: Biology and Chemistry*, 13, 204-209 (2005) and Price, Stacy E., et al., "Micellar Catalysis of Nitric Oxide Dissociation from Diazeniumdiolates" *Langmuir*, 19, 2096-2102 (2003), which are incorporated herein by reference in their entirety.

In particular embodiments of the present invention, the bath composition may controllably release nitric oxide when contacted with an aqueous solution and/or when one or more components of the bath composition are combined and contacted with an aqueous solution. The release of nitric oxide may be immediate upon contact with an aqueous solution and/or may begin after a certain duration of time. Nitric oxide may be released from the bath continuously and/or intermittently, for example, by exposure to repeated light/dark cycles. The release kinetics of the nitric oxide may be varied and/or tuned by changing the temperature and/or pH of the aqueous solution and/or bath. To decrease the release rate of nitric oxide, the temperature of the aqueous solution and/or bath may be decreased and/or the pH of the aqueous solution and/or bath may be increased. To increase the release rate of nitric oxide, the temperature of the aqueous solution and/or bath may be increased and/or the pH of the aqueous solution and/or bath may be decreased. In some embodiments of the present invention, the amount of nitric oxide released may be controlled by the concentration of NO-releasing compounds in the bath composition and/or by the amount of bath composition contacted with the aqueous solution and/or bath. For example, a high concentration of NO-releasing compounds in the bath composition and/or contacting a greater amount of the bath composition with the aqueous solution, may result in more nitric oxide released in the bath or soak.

In certain embodiments of the present invention, the amount of nitric oxide released increases over time, and after a certain amount of time, the amount of nitric oxide released may decrease. In some embodiments, the amount of nitric oxide released is substantially constant (i.e., on average varying less than about ±20%, ±15%, ±10%, or ±5%) over a period of time. In other embodiments of the present invention, the amount of nitric oxide released varies over the duration of the bath. The release of nitric oxide, in some embodiments, may occur in random and/or sequential releases of the same or varying concentration.

A bath composition of the present invention may be in any suitable form, including a powder, a bead, a granule, a tablet, a film, a coating, a film-coated tablet, and/or a polymer sheet. The polymers and/or solid compositions may or may not dissolve or break down in water. In some embodiments, polymeric compositions that may be used include those described in U.S. patent application Ser. No. 13/256,925, filed on Sep. 15, 2011, the contents of which are herein incorporated by reference in their entirety.

For example, as illustrated in FIG. 1, a bath/soak is provided as tablets that release nitric oxide in a concentrated area. An item, such as a foot, is placed in the bath with water and the tablets and the item is placed in proximity to the tablets to receive the nitric oxide released from the tablets. FIG. 2 illustrates an alternative embodiment where the nitric oxide releasing material is distributed throughout the bath/soak. As seen in FIG. 2, the item, such as a foot, is placed in the bath/soak with a composition, such as a powder, and water and the powder mixed throughout the water to release the nitric oxide throughout the bath.

The bath compositions of the present invention may be packaged and/or stored in a single dose unit and/or a multi-dose unit. One or more components of the bath composition may be packaged and/or stored separately from the other components of the bath composition in a single dose unit and/or a multi-dose unit. For example, in some embodiments of the present invention, the NO-releasing compounds may be packaged and/or stored separately from the other components of the bath composition, such as but not limited to an acid, until contacted with the aqueous solution. In other embodiments of the present invention, a pH modifying agent is packaged and/or stored separately from the other components of the bath composition. When separate, the one or more components of the bath composition may be contacted with an aqueous solution in any order. In another aspect of the present invention, the bath composition may be coated onto one or more interior surfaces of a vessel, such as, but not limited to, a disposable tub and/or a foot basin, and/or on one or more surfaces of an inert object, such as, but not limited to, a sponge, loofah, cloth, toy, and/or massager.

The bath composition may be packaged and/or stored in any manner. In certain embodiments of the present invention, the bath composition is packaged and/or stored such that the packaging minimizes contact with air, water, and/or light. Exemplary packages for the bath composition include, but are not limited to, a bottle, a plastic wrap or container, a foil sachet, a polyethylene sachet, and any combination thereof. In certain embodiments of the present invention, the packaging may be used as a vesicle or container in which to add the aqueous solution and/or the packaging may be used in the methods of treatment of the present invention.

In some embodiments, packaged bath compositions of the present invention may be provided with a shelf life of at least about one week. In further embodiments, the packaged bath compositions may have a shelf life of at least about four weeks, at least about 12 weeks, at least about 26 weeks, or at least about 52 weeks. In still further embodiments, the packaged bath compositions may have a shelf life of from at least about 12 to at least about 104 weeks, or any range and/or individual value therein. As used herein, the term "shelf life" refers to the length of time that the product (i.e., a bath composition of the present invention) maintains the ability to release a therapeutically effective amount of nitric oxide in an unopened package stored under recommended storage conditions. The shelf life may, for example, be evidenced by the "use by" of "best if used by" date for the product, the manufacturer's expiration date of the product and/or the actual product characteristics after the specified period of time. Accordingly, the term "shelf life" as used herein should be construed as including both an "actual" shelf life of the product and a "predicted" shelf life of the product unless stated otherwise. As one skilled in the art will recognize, the rate of release of nitric oxide in a bath composition described herein under packaged and/or stored conditions may be different (i.e., faster or slower) than the rate of release of nitric oxide when the bath composition is in use. In certain embodiments, the rate of release of nitric oxide may be faster when a bath composition is in use compared to the rate of release of nitric oxide when the bath composition was packaged and/or stored.

In some embodiments, the shelf life of the product is the time that the product maintains the ability to release at least 50% of the initial amount nitric oxide that the product may release when packaged. In further embodiments, the shelf life of the product is the time that the product maintains the ability to release at least 70%, at least 80%, at least 90%, at least 95%, or at least 98% of the initial amount nitric oxide that the product may release when packaged. In some embodiments, the recommended storage conditions are room temperature. In some embodiments, the recommended storage conditions are refrigerated storage conditions. In particular embodiments, the refrigerated storage conditions are in a range from about 1 to about 12° C.

Further embodiments may provide packaged bath compositions that have a useful life of at least about 7 days after opening the package. In further embodiments, the useful life may be at least about 30 days, at least about 60 days or at least about 90 days. In still further embodiments, the packaged bath compositions may have a useful life of from at least about 60 days to at least about 730 days, or any range and/or individual value therein. As used herein, the term "useful life" refers to the length of time that the product maintains the ability to release a therapeutically effective amount of nitric oxide from an opened packaged when applied as recommended and when stored under recommended storage conditions. The useful life may, for example, be evidenced by the manufacturer's recommended time to dispose of the product after opening or measurements of the products characteristics after opening. Accordingly, the term "useful life" as used herein should be construed as including both an "actual" useful life of the product and a "predicted" useful life of the product unless stated otherwise. In some embodiments, the useful life of the product is the time that the product maintains the ability to release at least 50% of the initial amount nitric oxide that the product may release when the package is opened. In further embodiments, the shelf life of the product is the time that the product maintains the ability to release at least 70%, at least 80%, at least 90%, at least 95%, or at least 98% of the initial amount nitric oxide that the product may release when the package is opened. In some embodiments, the recommended storage conditions after opening are room temperature. In particular embodiments, the recommended storage conditions after opening are refrigerated conditions.

A further aspect of the present invention provides methods of treating a subject by contacting a bath composition of the present invention with an aqueous solution, thereby producing a nitric oxide releasing bath, and exposing a portion of the subject to the bath. Thus, by exposing the subject to the nitric oxide bath, the subject may be treated with nitric oxide. The terms "treat", "treating", and grammatical variants thereof, as used herein in reference to treating a subject, refers to treating and/or inhibiting and/or protecting against a disease, disorder, infection, wound, and/or clinical symptom in a subject. The methods of the present invention may provide for the total absence of the disease, disorder, infection, wound, and/or clinical symptom in the subject. The methods of the present invention may also provide partial treatment, such as relieving and/or reducing the effects and/or severity of the disease, disorder, infection, wound, and/or clinical symptom in the subject and/or delaying the progression and/or onset of the disease, disorder, infection, wound, and/or clinical symptom compared to what would occur in the absence of the methods of the present invention.

The term "exposing" and grammatical variants thereof, as used herein in reference to the subject and the bath, refer to submerging; contacting, immersing, dipping, wetting, dousing, washing, rinsing, soaking, plunging, dunking, dampening, and/or placing any portion of the subject (e.g., one or more extremities, the whole body, etc.) into contact with the bath for any duration of time. In certain embodiments of the present invention, the subject is exposed to the bath for a time sufficient to obtain a treatment effective amount of nitric oxide. A "treatment effective" amount as used herein is an amount that is sufficient to treat (as defined herein) the subject. Those skilled in the art will appreciate that the therapeutic effects need not be complete or curative, as long as some benefit is provided to the subject.

The methods of the present invention may include modifying the release kinetics of the nitric oxide in the bath. As described above, the release kinetics of the nitric oxide may be varied and/or tuned by changing the temperature and/or pH of the aqueous solution and/or bath. To decrease the release rate of nitric oxide, the temperature of the aqueous solution and/or bath may be decreased and/or the pH of the aqueous solution and/or bath may be increased. To increase the release rate of nitric oxide, the temperature of the aqueous solution and/or bath may be increased and/or the pH of the aqueous solution and/or bath may be decreased. In some embodiments of the present invention, the amount of nitric oxide released may be controlled and/or changed by adding the same or varying amounts of the bath composition to the bath at various times throughout the duration of the bath. For embodiments wherein the temperature and/or bath is increased, any temperature that may suitably allow for the release of NO may be used, including, for example, temperatures in a range from about 25 or 30 to 40° C., or greater. In embodiments wherein the bath compositions are used for articles, devices and/or instruments, the temperature range may be much higher, such as, for example, in a range from about 30 to 40, 50, 60, 70 80, 90, 100° C., or greater.

The present invention finds use in both veterinary and medical applications, including drug evaluation and drug development purposes. Suitable subjects of the present invention include, but are not limited to avians and mammals. The term "avian" as used herein includes, but is not limited to, chickens, ducks, geese, quail, turkeys, pheasants, ratites (e.g., ostrich), parrots, parakeets, macaws, cockatiels, canaries, finches, and birds in ovo. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), and mammals in utero. In some embodiments of the present invention, the subject is a mammal and in certain embodiments the subject is a human. Human subjects include both males and females and subjects of all ages including fetal, neonatal, infant, juvenile, adolescent, adult, and geriatric subjects. Subjects may be treated for any purpose, such as, but not limited to, treatment and/or prevention of infection.

In particular embodiments of the present invention, the methods of the present invention are used to treat a dermatological condition, wound, burn, and any combination thereof. Exemplary dermatological conditions include, but are not limited to; atopic dermatitis, contact dermatitis, chicken pox, psoriasis, impetigo, secondary skin infections, bed sores, diabetic foot ulcers, venous leg ulcers, burns, surgical incisions, acne vulgaris, truncal acne and/or cystic nodular acne, onychomycosis, tinea pedis, tinea cruris, tinea capitis, molluscum contagiosum, common and genital warts, and any combination thereof. Bath compositions according to embodiments of the invention may be used to treat other skin ailments, either via anti-microbial action, anti-inflammatory action, or by any other mechanism.

In addition to dermatological conditions, the present invention could also be utilized to treat pain, inflammation or other conditions affected by nitric oxide delivery. For example, a nitric oxide-releasing bath or soak could be used to treat arthritis, tendonitis, plantar facitis, sprains, sports injuries, repetitive motion injuries, such as carpal tunnel syndrome or muscle overuse.

Such methods may be used in combination with any other known methods of wound treatment, including the application of other therapeutic agents, such as those that have anti-inflammatory, pain-relieving, immunosuppressant, vasodilating, wound healing and/or anti-biofilm forming properties. For the methods used herein, additional therapeutic agents and methods may be used prior to, concurrently with or after contact with the bath compositions of the present invention.

In some embodiments of the present invention, bath compositions may be used to deliver NO to articles, devices and/or instruments, for example, to clean, disinfect, decrease the microbial burden and/or decrease or remove biofilms. For example, in some embodiments, a bath composition described herein may be used to clean or disinfect medical or surgical instruments. The term "instrument" is intended to be defined broadly, to include any items, objects, implements or devices. Simply by way of example and without limitation, instruments may be implements employed in patient or client contact (human or veterinary) during the practice of surgery, medicine, dentistry, podiatry, pathology for e.g., therapeutic, diagnostic and/or research purposes. Examples include, but are not limited to, surgical instruments, e.g., scalpels, probes, clamps, etc., endoscopes, operating room or dental hand pieces, ventilation tubes, and the like. Surgical instruments and equipment inevitably pick up amounts of bio-burden on them after being employed in operations on humans or animals. Surgical instruments include, for example, rigid and flexible scopes, laparoscopic instruments, trays and anything that may have contact, directly or indirectly, with a patient or subject.

As another example, bath compositions described herein may be used to clean/disinfect articles implanted or otherwise associated with a subject, including contact lenses, implantable medical devices, dental implants and appliances, dentures, and the like.

Other devices that may be subjected to the bath compositions also include, but are not limited to, miscellaneous other instruments and/or implements employed in cosmetic and beauty applications. These applications include hair cutting, nail care, body art, skin piercing, collection of body fluids, and the like. The bath compositions according to embodiments of the invention are also contemplated to be useful for cleaning implements and items employed in the food processing and pharmaceutical industries.

The articles, devices and/or instruments may be combined with an NO-releasing bath solution by any suitable method, including using the NO-releasing bath solutions alone, or with other washes and agents. Other cleaning solutions may be used in combination or they may be used in sequential rinse/cleaning cycles. Water rinsing or soaking may also be performed before and/or after contact with the NO-releasing bath solutions.

In some embodiments, bath compositions according to an embodiment of the invention may also be used in aqueous solutions that are applied or in contact with plants, including trees, flowers, herbs, bushes, grasses, vines, ferns, mosses, green algae and the like. The term "plant" includes any living organism in the kingdom Plantae, including common and exotic plant varieties. In particular embodiments, the NO-releasing bath solutions may be used with cut plants to prolong life in vases, potters, and the like.

The invention will now be described further with respect to the foregoing examples. It should be appreciated that these examples are for the purpose of illustrating the invention, and do not limit the scope of the invention as defined by the claims

EXAMPLES

Tables 1 through 3 illustrate particular exemplary bath/soak formulations according to some embodiments of the present invention. Table 1 illustrates three possible effervescent formulations. Table 2 illustrates three possible non-effervescent formulations. Table 3 illustrates three possible bath salt formulations. Nitricil™ is a NO-releasing co-condensed silica, from Novan, Inc. and may be provided with one or more different release profiles and/or functional groups, such as, but not limited to, diazeniumdiolate-functionalized co-condensed silica.

TABLE 1

Proposed Effervescent Formulations

| Ingredient | % w/w | | |
|---|---|---|---|
| Nitricil ™ | 50.0 | 50.0 | 50.0 |
| Sodium bicarbonate | 40.0 | — | 40.0 |
| Potassium carbonate | — | 40.0 | — |
| Citric acid, anhydrous | 10.0 | 10.0 | 5.0 |
| Tartaric acid | — | — | 5.0 |
| % Total | 100.0 | 100.0 | 100.0 |

TABLE 2

Proposed Non-Effervescent Formulations

| Ingredient | % w/w | | |
|---|---|---|---|
| Nitricil ™ | 50.0 | 50.0 | 50.0 |
| Colloidal oatmeal | 42.9 | 44.9 | 42.7 |
| Citric acid, anhydrous | 5.0 | — | 5.0 |
| Sodium dodecyl sulfate | 2.0 | 5.0 | 2.0 |
| Menthol | 0.1 | 0.1 | — |
| Camphor | — | — | 0.3 |
| % Total | 100.0 | 100.0 | 100.0 |

TABLE 3

Proposed Bath Salt Formulations

| Ingredient | % w/w | | |
|---|---|---|---|
| Nitricil ™ | 50.0 | 50.0 | 50.0 |
| Magnesium sulfate | 49.9 | 49.5 | 42.5 |
| Citric acid, anhydrous | — | — | 7.0 |
| Menthol | 0.1 | — | 0.5 |
| Camphor | — | 0.5 | — |
| % Total | 100.0 | 100.0 | 100.0 |

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A bath composition comprising:
   sodium bicarbonate at a concentration in a range from about 30% to about 60% by weight of the bath composition;
   citric acid and/or tartaric acid at a concentration in a range from about 0.1% to about 5% by weight of the bath composition; and
   at least one nitric oxide (NO)-releasing compound, wherein the at least one NO-releasing compound comprises a NO-releasing macromolecule comprising diazeniumdiolate-functionalized co-condensed silica at a concentration in a range from about 35% to about 65% by weight of the bath composition, wherein the diazeniumdiolate-functionalized cocondensed silica has a half-life of greater than about 60 minutes at 37° C. and pH 7.4, and wherein the bath composition provides a total NO release of about 1 mmol NO/L to about 100 mmol NO/L.

2. The bath composition of claim 1, wherein the at least one NO-releasing compound releases NO upon reaction with water.

3. The bath composition of claim 1, wherein the concentration of the diazeniumdiolate-functionalized co-condensed silica is in a range from about 35% to about 55% by weight of the bath composition.

4. The bath composition of claim 1, wherein the sodium bicarbonate is present at a concentration in a range from about 35% to about 50% by weight of the bath composition.

5. The bath composition of claim 1, wherein the citric acid and/or tartaric acid is present at a concentration in a range from about 0.2% to about 2% by weight of the bath composition.

6. The bath composition of claim 1, further comprising an aromatherapy agent, wherein the concentration of the aromatherapy agent is in a range from about 0.1% to about 10% by weight of the bath composition.

7. The bath composition of claim 1, further comprising a glidant, wherein the concentration of the glidant is in a range from about 0.1% to about 10% by weight of the bath composition.

8. The bath composition of claim 1, further comprising an inert filler, wherein the concentration of the inert filler is in a range from about 0.1% to about 60% by weight of the bath composition.

9. The bath composition of claim 1, wherein the diazeniumdiolate-functionalized co-condensed silica has an octanol/water partition coefficient in a range from 0.1 to 7.

10. The bath composition of claim 1, wherein the diazeniumdiolate-functionalized co-condensed silica is present as particles and the particles have a hydrodynamic radius in a range from about 1 nm to about 10 microns.

11. The bath composition of claim 1, wherein the diazeniumdiolate-functionalized co-condensed silica is present as particles and the nitric oxide storage of the diazeniumdiolate-functionalized co-condensed silica particles is in a range from about 0.1 pmol NO/g to about 1 mmol NO/g of the bath composition.

12. The bath composition of claim 1, wherein the bath composition is in the form of a powder, a bead, a granule, a tablet, a film, a coating, a film-coated tablet, a polymer sheet, and any combination thereof.

13. The bath composition of claim 1, wherein the composition further comprises at least one compound that provides a visual indicator of when NO, nitrous acid and/or salts thereof are present.

14. A method of treating a subject comprising: contacting the bath composition of claim 1 with an aqueous solution to form NO, thereby producing a nitric oxide releasing bath, and exposing at least a portion of the subject to the bath.

15. The method of claim 14, further comprising adjusting the release rate of the NO by changing the temperature of the bath and/or modifying the pH of the bath.

16. The bath composition of claim 6, wherein the aromatherapy agent is selected from menthol and/or camphor.

17. The bath composition of claim 7, wherein the glidant is selected from colloidal silicon dioxide and/or talc.

18. The bath composition of claim 8, wherein the inert filler is selected from microcrystalline cellulose and/or lactose.

19. The bath composition of claim 1, wherein the bath composition is present as a coating on a surface of a container.

* * * * *

UNITED STATES PATENT AND TRADEMARK OFFICE
CERTIFICATE OF CORRECTION

PATENT NO. : 9,669,041 B2
APPLICATION NO. : 14/353599
DATED : June 6, 2017
INVENTOR(S) : Stasko et al.

Page 1 of 1

It is certified that error appears in the above-identified patent and that said Letters Patent is hereby corrected as shown below:

In the Claims

Column 21, Claim 1, Line 3: Please correct "cocondensed silica" to read -- co-condensed silica --

Signed and Sealed this
Twenty-fourth Day of April, 2018

Andrei Iancu
*Director of the United States Patent and Trademark Office*